US00PP16723P2

(12) United States Plant Patent
Miyazaki et al.

(10) Patent No.: US PP16,723 P2
(45) Date of Patent: Jun. 27, 2006

(54) ***PHLOX* PLANT NAMED 'SUNPHLOCHEBU'**

(50) Latin Name: *Phlox drummondii*
Varietal Denomination: Sunphlochebu

(75) Inventors: Kiyoshi Miyazaki, Shiga (JP); Yasuyuki Murakami, Shiga (JP); Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 61 days.

(21) Appl. No.: 11/091,832

(22) Filed: Mar. 28, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Sunphlochebu', characterized by its upright, outwardly spreading and mounded plant habit; freely branching and vigorous growth habit; freely and continuous flowering habit; white to light pink-colored flowers with red purple-colored centers; tolerance to high temperatures; and good garden performance.

1 Drawing Sheet

Botanical designation: *Phlox drummondii.*
Cultivar denomination: 'Sunphlochebu'.

BACKGROUND OF THE INVENTION

The present Invention relates to a new and distinct cultivar of *Phlox* plant, botanically known as *Phlox drummondii*, and hereinafter referred to by the cultivar name Sunphlochebu.

The new *Phlox* is a naturally-occurring branch mutation of an unnamed proprietary selection of *Phlox drummondii*, not patented. The new *Phlox* was discovered and selected by the Inventors from within a population of plants of the parent selection in a controlled environment in Higashiomi, Shiga, Japan in April, 2001.

Asexual reproduction of the new cultivar by terminal cuttings at Higashiomi, Shiga, Japan since October, 2003, has shown that the unique features of this new *Phlox* are stable and reproduced true to type in successive generations.

SUMMARY OF THE INVENTION

Plants of the cultivar Sunphlochebu have not been observed under all possible environmental conditions. The phenotype may vary somewhat with variations in environment such as temperature and light level without, however, any variance in genotype.

The following traits have been repeatedly observed and are determined to be the unique characteristics of 'Sunphlochebu'. These characteristics in combination distinguish 'Sunphlochebu' as a new and distinct cultivar of *Phlox:*

1. Upright, outwardly spreading and mounded plant habit.
2. Freely branching and vigorous growth habit.
3. Freely and continuous flowering habit.
4. White to light pink-colored flowers with red purple-colored centers.
5. Tolerant to high temperatures.
6. Good garden performance.

Plants of the new *Phlox* can be compared to plants of the parent selection. In side-by-side comparisons conducted in Higashiomi, Shiga, Japan, plants of the new *Phlox* differed from plants of the parent selection primarily in flower color as plants of the parent selection have red purple-colored flowers.

Plants of the new *Phlox* can be compared to the *Phlox drummondii* cultivar Parona Rose with Eye, not patented. In side-by-side comparisons conducted in Higashiomi, Shiga, Japan, plants of the new *Phlox* differed from plants of the cultivar Parona Rose with Eye in the following characteristics:

1. Plants of the new *Phlox* were shorter but broader than plants of the cultivar Parona Rose with Eye.
2. Plants of the new *Phlox* were more vigorous than plants of the cultivar Parona Rose with Eye.
3. Plants of the new *Phlox* were more freely branching than plants of the cultivar Parona Rose with Eye.
4. Plants of the new *Phlox* had smaller leaves than plants of the cultivar Parona Rose with Eye.
5. Plants of the new *Phlox* were more freely flowering than plants of the cultivar Parona Rose with Eye.
6. Plants of the new *Phlox* flowered from April to late October in Japan whereas plants of the cultivar Parona Rose with Eye flowered from April to June in Japan.
7. Plants of the new *Phlox* and the cultivar Parona Rose with Eye differed in petal coloration as plants of the cultivar Parona Rose with Eye had red purple-colored petals.
8. Plants of the new *Phlox* did not produce seeds whereas plants of the cultivar Parona Rose with Eye produced seeds.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox*.

The photograph at the top of the sheet is a side perspective view of a typical plant of 'Sunphlochebu'.

The photograph at the bottom of the sheet is a close-up view of typical flowers and leaves of 'Sunphlochebu'.

DETAILED BOTANICAL DESCRIPTION

The aforementioned photographs, following observations and measurements describe plants grown in Higashiomi, Shiga, Japan in an outdoor nursery and under commercial production practices during the spring and summer. Plants were grown in 15-cm containers and were about four months old when the photographs and description were taken. During the production of the plants, day temperatures averaged 22° C. and night temperatures averaged 12° C. Plants were pinched one time in the spring. In the following description, color references are made to The Royal Horticultural Society Colour Chart, 2001 Edition, except where general terms of ordinary dictionary significance are used.

Botanical classification: *Phlox drummondii* cultivar Sunphlochebu.

Parentage: Naturally-occurring branch mutation of an unnamed proprietary selection of *Phlox drummondii*, not patented.

Propagation:

*Type*.—By terminal cuttings.

*Time to initiate roots*.—About two to three weeks at 20 to 25° C.

*Time to produce a rooted plant*.—About one to two months at 20 to 25° C.

*Root description*.—Fine, fibrous, fleshy; ivory to pale brown in color.

*Rooting habit*.—Freely branching.

Plant description:

*Plant form/habit*.—Upright, outwardly spreading and mounded plant habit; broadly inverted triangle; vigorous growth habit. Freely branching habit with short internodes, dense and bushy growth habit.

*Plant height*.—About 16.6 cm.

*Plant width* (*spread*).—About 42.4 cm.

*Lateral branches*.—Length: About 20.6 cm. Diameter: About 1.4 mm. Internode length: About 1.6 cm. Strength: Strong. Texture: Pubescent. Color: 144A.

*Foliage description*.—Arrangement: Alternate, simple; sessile. Length: About 2.7 cm. Width: About 9 mm. Shape: Lanceolate. Apex: Acute. Base: Cordate. Margin: Entire. Texture, upper and lower surfaces: Pubescent. Venation pattern: Pinnate; reticulate. Color: Developing and fully expanded leaves, upper surface: 137B; venation, similar to lamina. Developing and fully expanded leaves, lower surface: 138B; venation, similar to lamina.

Flower description:

*Flower type/habit*.—Single, rounded salverform flowers arranged in terminal and lateral cymes; flowers face upright and outward. Freely flowering habit with about five flowers per inflorescence.

*Fragrance*.—Present; typical of *Phlox*.

*Natural flowering season*.—Continuously flowering from April to late October in Japan. Flowers not persistent.

*Postproduction longevity*.—Flowers last about five days on the plant.

*Inflorescence height*.—About 5.3 cm.

*Inflorescence diameter*.—About 5.9 cm.

*Flower buds*.—Height: About 1.4 cm. Diameter: About 3 mm. Shape: Clavate. Color: 1D.

*Flowers*.—Diameter: About 2.8 cm. Depth: About 1.4 cm.

*Petals*.—Quantity per flower: Five in a single whorl; imbricate; petals fused at the base into a narrow tube. Lobe length: About 1.3 cm. Lobe width: About 1.3 cm. Shape: Broadly rhombic. Apex: Cuspidate. Margin: Entire. Aspect: Mostly flat. Texture, upper and lower surfaces: Smooth, glabrous. Color: Developing petals, upper surface: N155B; towards the base, 72A. Developing petals, lower surface: N155B to 69C. Fully expanded petals, upper surface: N155B becoming closer to 65C with development; towards the base, 72A to 73A. Fully expanded petals, lower surface: N155B to 69C.

*Sepals*.—Quantity per flower: Typically five in a single whorl, fused; narrow tubular calyx. Length: About 3.8 mm. Width: About 0.7 mm. Shape: Lanceolate. Apex: Acute. Texture, upper and lower surfaces: Smooth, glabrous. Color, immature, upper and lower surfaces: 137A. Color, mature, upper and lower surfaces: 137A.

*Pedicels*.—Length: About 9 mm. Diameter: About 0.4 mm. Texture: Pubescent. Color: 177B.

*Reproductive organs*.—Stamens: Quantity per flower: Typically five. Anther shape: Linear. Anther length: About 1 mm. Anther color: 12A. Pollen amount: Moderate. Pollen color: 12A. Pistils: Quantity per flower: Typically one. Stigma shape: Tri-parted. Stigma color: 1C. Style length: About 0.3 mm. Style color: 1C. Ovary color: 144A.

*Seed/fruit*.—Seed and fruit development have not been observed.

Disease/pest resistance: Plants of the new *Phlox* have not been noted to be resistant to specific pathogens and pests common to *Phlox*.

Garden performance: Plants of the new *Phlox* have been observed to have good garden performance and tolerate rain, wind and tolerated temperatures from 0 to 35° C.

It is claimed:

1. A new and distinct cultivar of *Phlox* plant named 'Sunphlochebu', as illustrated and described.

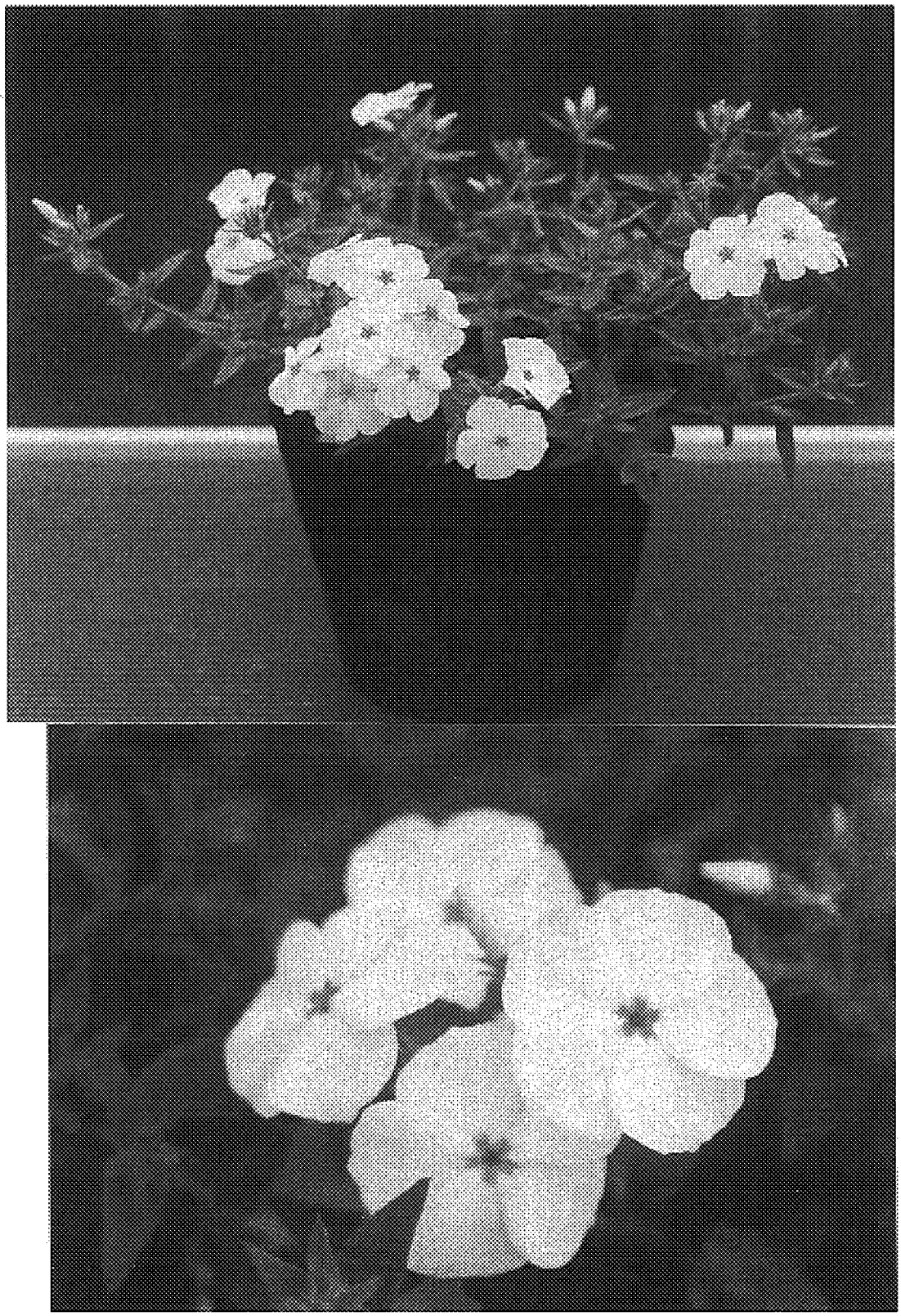

* * * * *